(12) United States Patent
Yano et al.

(10) Patent No.: US 8,012,749 B2
(45) Date of Patent: Sep. 6, 2011

(54) METHODS FOR THE PRODUCTION OF HEMAGGLUTINATING VIRUS OF JAPAN AND ADENOVIRUS USING CULTURED CELLS

(75) Inventors: Takahiro Yano, Hiratsuka (JP); Tetsuji Nagasawa, Ikeda (JP); Akiko Temma, Suita (JP); Naho Suzuki, Itami (JP); Kazue Miyaji, Ikeda (JP)

(73) Assignee: GenomIdea, Inc., Ibaraki-shi, Osaka (JP)

( * ) Notice: Subject to any disclaimer, the term of this patent is extended or adjusted under 35 U.S.C. 154(b) by 448 days.

(21) Appl. No.: 12/083,126

(22) PCT Filed: Oct. 4, 2006

(86) PCT No.: PCT/JP2006/319849
§ 371 (c)(1),
(2), (4) Date: Jul. 30, 2008

(87) PCT Pub. No.: WO2007/040242
PCT Pub. Date: Apr. 12, 2007

(65) Prior Publication Data
US 2008/0318299 A1 Dec. 25, 2008

(30) Foreign Application Priority Data
Oct. 5, 2005 (JP) ................................. 2005-292045

(51) Int. Cl.
C12N 5/00 (2006.01)
C12N 7/00 (2006.01)
(52) U.S. Cl. ..................................... 435/325; 435/235.1
(58) Field of Classification Search .......................... None
See application file for complete search history.

(56) References Cited

U.S. PATENT DOCUMENTS
5,952,227 A 9/1999 Kim et al.
6,210,922 B1 * 4/2001 Cote et al. .................... 435/69.1

FOREIGN PATENT DOCUMENTS
JP 8-242848 9/1996
JP 10-66563 3/1998
JP 2001-286282 10/2001
JP 2003219866 8/2003
JP 2004-283097 10/2004
WO WO 97/30147 8/1997

OTHER PUBLICATIONS

Sakaguchi, T.. et al., AIP1/Alix Is a Binding Partner of Sendai Virus C Protein and Facilitates Virus Budding J. Virol. 2005 79: 8933-8941.*

Virus Experimental Protocols, Medical View Co., Ltd., pp. 68-78 (1995).
European Search Report for EP 06 81 1189 completed on Jan. 21, 2009.
Cote, et al., "Serum-Free Production of Recombinant Proteins and Adenoviral Vectors by 293SF-3F6 Cells," *Biotechnology and Bioengineering* 59(5):567-575 (Sep. 1998).
Garnier, et al., "Scale-up of the adenovirus expression system for the production of recombinant protein in human 293S cells," *Cytotechnology* 15:145-155 (1994).
Heylbroeck, et al., "The IRF-3 Transcription Factor Mediates Sendai Virus-Induced Apoptosis," *J. Virology* 74(8):3781-3792 (Apr. 2000).
Wang, et al., "A20 is a potent inhibitor of TLR-3 and Sendai virus-induced activation of NF-κB and ISRE and IFN-β promoter," *FEBS Letters* 576:86-90 (2004).
Xanthoudakis, et al., "Transient Expression of the Beta Interferon Promoter in Human Cells," Molecular and Cellular Biol. 7(10):3830-3835 (Oct. 1987).
International Search Report for PCT/JP2006/319849 filed Oct. 4, 2006.
English translation International Preliminary Report on Patentability for for PCT/JP2006/319849 filed Oct. 4, 2006.
English translation Written Opinion of the International Searching Authority for for PCT/JP2006/319849 filed Oct. 4, 2006.
Cassidy, et al., "The Sialic Acids," *J. Biol. Chem.* 240(9):3501-3506 (Sep. 1965).
English language abstract for JP 8-242848, listed as document B1 above, 1996.
English language abstract for JP 10-66563, listed as document B2 above, 1998.
English language abstract for JP 2001-286282, listed as document B3 above, 2001.
English language abstract for JP 2003-219866, listed as document B4 above, 2003.
English language abstract for JP 2004-283097, listed as document B5 above, 2004.

* cited by examiner

*Primary Examiner* — Mary E Mosher
*Assistant Examiner* — Myron Hill
(74) *Attorney, Agent, or Firm* — Law Office of: Michael A. Sanzo, LLC

(57) ABSTRACT

A novel cell suited for mass production of Hemagglutinating Virus of Japan (HVJ), a method for obtaining the cell and use of the cell are disclosed. The human cell is originated from a transformed human kidney cell line, the doubling time thereof in logarithmic growth phase in suspension culture in a serum-free medium is not more than 40 hours, the cell has a freeze-recovery property, the maximum density of viable cells in suspension culture is not less than $10^6$ cells/mL, and HVJ can grow in the cell. The method for obtaining the human cell comprises the steps of suspension-culturing a human transformed kidney cell line in a serum-free medium, and cloning the grown cells; and selecting, from the cloned cells, a cell whose doubling time in logarithmic growth phase in suspension culture in a serum-free medium is not more than 40 hours, which has a freeze-recovery property, whose maximum density of viable cells in suspension culture is not less than $10^6$ cells/mL, in which HVJ can grow.

10 Claims, 4 Drawing Sheets

METHODS FOR THE PRODUCTION OF HEMAGGLUTINATING VIRUS OF JAPAN AND ADENOVIRUS USING CULTURED CELLS

CROSS REFERENCE TO RELATED APPLICATIONS

The present application is U.S. national stage of international application PCT/JP2006/319849, which had an international filing date of Oct. 4, 2006, and which was published in Japanese under PCT Article 21(2) on Apr. 12, 2007. The international application claims priority to Japanese application 2005-292045, filed on Oct. 5, 2005. These prior applications are hereby incorporated by reference in their entirety.

TECHNICAL FIELD

The present invention relates to an isolated human cell which is suited as a host cell for producing virus such as Hemagglutinating Virus of Japan (hereinafter referred to as "HVJ") or a foreign gene product, as well as a method for obtaining the cell and use of the cell.

BACKGROUND ART

HVJ is a kind of mouse pneumonia viruses and is not infectious to human. It has two types of glycoproteins (F and HN) on its cell-fusing viral outer membrane, and the proteins have the ability to fuse two types of cells (cell fusion). In recent years, a technique using the envelope of HVJ as a vector (HVJ envelope vector) was developed and has been commercialized (Patent Literature 1). The envelope of HVJ is used as the HVJ envelope vector after removing the genomic RNA of HVJ. A desired foreign gene is encapsulated in the envelope and the virus is infected to cultured cells or an organ so as to transfect the desired gene into the cells. Since the genomic RNA of the virus has been removed, the HVJ envelope is highly safe. Since the envelope has an ability to fuse cells, the efficiency of transfection into the cell is high. A large amount of foreign genes can be encapsulated, and the host spectrum of the virus is wide. Therefore, it is expected that the vector will be more and more widely used as a tool for analyzing gene function and as a vector for gene therapy.

Mass production of HVJ is conventionally carried out by inoculating HVJ to chicken eggs and growing the virus (see Virus Experimental Protocols, Medical View Co., Ltd., 1995, 68-78). However, with this method, there is a possibility that a highly immunogenic protein such as egg white albumin or the like or other impurities originated from the chicken egg may be contaminated in the recovered HVJ. Therefore, WHO recommends not to use chicken eggs but to use human cultured cells. When chicken eggs are used as a host, the inoculation operation of the virus and the recovery operation of the virus after growth thereof are complicated, so that the throughput is limited. To solve these problems, it is thought to grow HVJ using mammalian cultured cells in place of chicken eggs. Since mammals are the proper hosts of HVJ, HVJ can grow in various mammalian cells. However, no mammalian cultured cells which are suited for the mass production of HVJ are known.

Patent Literature 1: JP 2001-286282 A

Non-patent Literature 1: Virus Experimental Protocols, Medical View Co., Ltd., 1995, 68-78

DISCLOSURE OF THE INVENTION

Problems which the Invention Tries to Solve

An object of the present invention is to provide a novel isolated human cell suited for the mass production of HVJ, as well as a method for obtaining the cell and use of the cell.

Means for Solving the Problems

As a condition for the cell to be suited as a host cell for the production of HVJ, the present inventors set a condition that the cell can be grown in a serum-free medium. If the cell can be grown in a serum-free cell, the possibility that the recovered HVJ is contaminated with a substance originated from the serum, such as serum albumin, can be eliminated, which is advantageous. The present inventors also thought that it is advantageous to use a cell which can be grown in a bioreactor, that is to use a cell which can be suspension-cultured in a liquid culture medium. Further, the present inventors thought that it is advantageous if the cell density in the liquid medium can be made high and the cell has a high growing ability. The present inventors still further thought that it is advantageous for the ease of handling, storage, transportation and the like, if the cell can grow even if it is once frozen and then thawed. The present inventors still further thought that since gene therapy and analysis of gene function are mainly performed on human, a human cell is advantageous. The present inventors intensively studied to obtain a human cell which satisfies these various conditions. As a result, the present inventors succeeded in obtaining a human cell satisfying the above-described various conditions by selecting and cloning a cell under various conditions employing a human transformed kidney cell line as a parent cell, thereby completing the present invention.

That is, the present invention provides an isolated human cell originated from a transformed human kidney cell line, whose doubling time in logarithmic growth phase in suspension culture in a serum-free medium is not more than 40 hours, which has a freeze-recovery property, whose maximum density of viable cells in suspension culture is not less than $10^6$ cells/mL, and in which HVJ can grow. The present invention also provides a method for obtaining a human cell, the method comprising the steps of suspension-culturing a human transformed kidney cell line in a serum-free medium, and cloning the grown cells; and selecting, from the cloned cells, a cell whose doubling time in logarithmic growth phase in suspension culture in a serum-free medium is not more than 40 hours, which has a freeze-recovery property, whose maximum density of viable cells in suspension culture is not less than $10^6$ cells/mL, in which HVJ can grow. The present invention still further provides a method of producing a virus, the method comprising inoculating a desired virus to the isolated human cell according to the present invention; growing the virus in the cell; and recovering the grown virus.

Effects of the Invention

By the present invention, an isolated human cell which is suited for mass production of HVJ was first provided. Since the isolated human cell according to the present invention can be grown in a serum-free medium, there is no possibility that the recovered virus is contaminated with a substance originated from serum, when a virus such as HVJ is grown using the cells as a host and the virus is recovered. Further, since the isolated human cell according to the present invention can be grown by suspension culture in a liquid medium, since the growth rate is high, and since the cell can be cultured at a high density, the cell is suited for the mass production of a virus using a bioreactor. Still further, since the cell has a freeze-recovery property, storage and transportation of the cells are convenient.

BRIEF DESCRIPTION OF THE DRAWINGS

FIG. 1 shows the results when the cells were cultured for a long period of time using T6 and HyQ which showed high growing ability, thereby proceeding the acclimatization of the cells to a serum-free medium. VC means viable cells, and % means the survival rate.

FIG. 2 shows the results of the measurement of the HVJ production by FFU test carried out by the method wherein an aliquot of the single clones during cloning were sampled on a 96-well plate, trypsin (final concentration: 2 μg/mL) and HVJ (multiplicity of infection; MOI=23) were added thereto, the cells were cultured at 34° C. in a 5% $CO_2$ incubator for 3 days, and the supernatant was recovered. The numbers below the abscissa indicate clone numbers.

FIG. 3 shows the results obtained using the two clones (Clone A and Clone B) which showed high growing ability and productivity. Independent experiments were performed 3 times, and the results of the respective experiments are shown.

FIG. 4 shows the comparison between the gene transfection activity of HVJ produced by the two clones (Clone A and Clone B) which showed high growing ability and productivity, after removing impurities by purifying the harvest material. As a control for comparison, the HVJ (Egg) grown in an egg and purified in the same manner was also tested simultaneously. Independent experiments were performed 3 times, and the results of the respective experiments are shown.

BEST MODE FOR CARRYING OUT THE INVENTION

Figure 1:
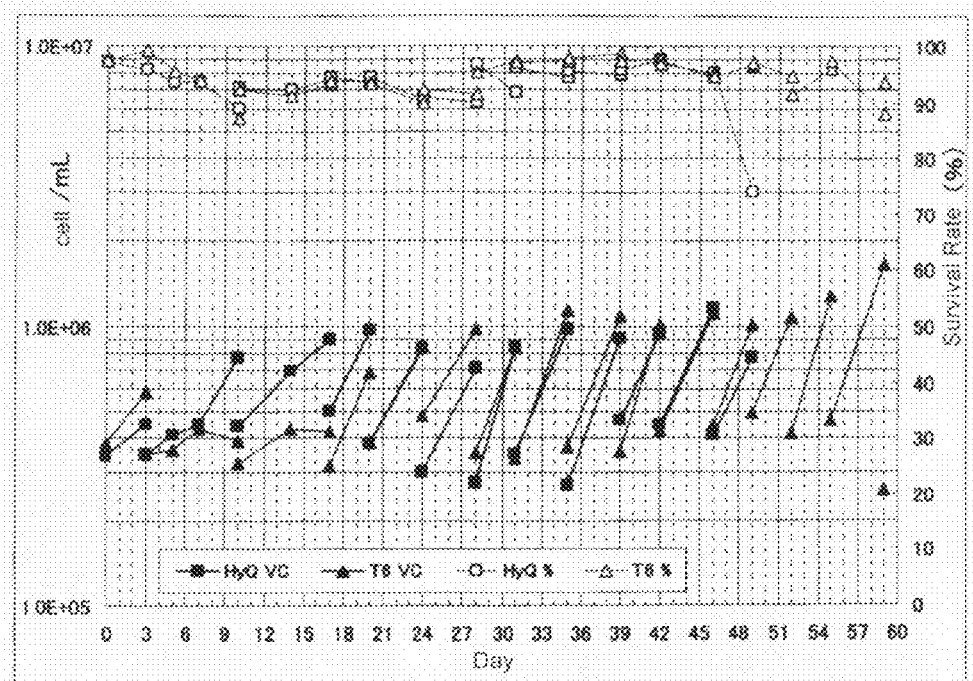
FIG. 1 Acclimatization of Cells to Serum-free Medium.

The isolated human cell according to the present invention is originated from a transformed human kidney cell line, preferably originated from 293 cell. The 293 cell (also called "HEK 293 cell", (HEK is the abbreviation of human embryonic kidney)) is widely used as the cell for producing adenovirus vectors, AAV vectors (adeno-associated virus vector), recombinant proteins and the like. The 293 cell is available from public depositaries such as Health Science Research Resources Bank and ATCC, and is also commercially available, so that it is easily available.

The isolated human cell according to the present invention can be grown by suspension culture in a serum-free medium. As the serum-free medium, those commercially available from various companies, such as T6 medium used in the Example below, and known serum-free media for 293 cell may be used. T6 medium is commercially available from JRH Biosciences, Lenexa, Kans., U.S., and contains 1.1 mg/L of a recombinant protein, plant hydrolysates, 0.1% of Pluronic F-68 (trade name, surfactant produced by BASF), 6.0 g/L of glucose, 1.8 g/L of sodium hydrogen carbonate, hypoxanthine and thymidine.

The isolated human cell according to the present invention has a doubling time in logarithmic growth phase in suspension culture in a serum-free medium of not more than 40 hours. The doubling time in logarithmic growth phase can be measured by measuring, with time, the number of cells in a unit volume of the medium, and calculating the time required for the number of cells to be doubled in logarithmic growth phase (the stage in which the number of cells is logarithmically increased, that is, the stage wherein the relationship between the common logarithm of the number of cells taken along the ordinate and the time taken along the abscissa is linear). The doubling time is the doubling time under conditions in which the cells well grow, such as, for example, in suspension culture in a culture medium suited for the growth of 293 cells, such as the above-described T6 medium, at 36.5° C., under 5-10% $CO_2$, and preferably the doubling time in a gyratory culture at 100-120 rpm. The doubling time in logarithmic growth phase is preferably 25 hours to 30 hours in a suspension culture at 36.5° C. under 5-10% $CO_2$.

The isolated human cell according to the present invention has a freeze-recovery property. The "freeze-recovery property" herein means that the cell can grow even after once frozen and then thawed. The cells grown after freezing have the growing ability and various characteristics such as productivity of HVJ, defined in the present invention.

The isolated human cell according to the present invention attains a maximum density of viable cells in suspension culture of not less than $10^6$ cells/mL. The "maximum density of viable cells" herein means that when the cells are cultured under appropriate conditions, the density of viable cells reach $10^6$ cells/mL or more at least one time point after initiation of the culturing. The "appropriate conditions" may be, for example, in suspension culture in a culture medium suited for the growth of 293 cells, such as the above-described T6 medium, at 36.5° C., under 5-10% $CO_2$, and preferably in a gyratory culture at 100-120 rpm. Preferably, the maximum density of viable cells in a suspension culture at 36.5° C., under 5-10% $CO_2$ is $2\times10^6$ cells/mL to $10^7$ cells/mL. The density of viable cells in the culture medium can be easily measured by manually counting the number of cells under the microscope using a hemacytometer, or by using a commonly used commercially available automated cell viability analyzer.

The isolated human cell according to the present invention is one in which HVJ can grow. Preferably, the growth of HVJ can attain a focus-forming unit (FFU) of not less than 108 FFU/mL, more preferably a focus-forming unit of not less than $6\times10^8$ FFU/mL to $5\times10^9$ FFU/mL. The "focus-forming unit" can be measured by a known FFU test (fluorescent antibody method: Quantification of infectious HVJ is carried out by counting the number of infected cells) (reference: Virus Experimental Protocols, Medical View Co., Ltd., 1995, 68-78; The sialic acids J. Biol. Chem., 240, 3501 (1965)), and a concrete method is described in Example below. Although the conditions under which HVJ is grown are not restricted, the preferred conditions are those wherein the cell density is $10^6$ cells/mL to $4\times10^6$ cells/mL; a medium for infection supplemented with sodium butyrate (final concentration 1-4 mM), and Factor-Xa (final concentration 0.05-2 U/mL) or trypsin (final concentration 2-8 µg/mL) is added to a concentration of 30 to 50%; HVJ virus solution is added at MOI=1-10; and the culturing is carried out at 30 to 34° C. for 40 to 72 hours. More preferred conditions are, for example, those wherein the sodium butyrate concentration is 2 mM and the culturing is carried out at 32° C. for 42 hours; or wherein the sodium butyrate concentration is 0 mM and the culturing is carried out at 34° C. for 72 hours. As concretely described in the Example below, to select the cells having a high ability to grow HVJ, the cells showing a high growing ability in the culturing in a well of a microplate may be primarily selected, and then the cells showing a high growing ability under suspension culture may be secondarily selected.

The isolated human cell according to the present invention is preferably one which can be subcultured maintaining the above-described characteristics, more preferably, one which can be subcultured for a long period of time of not less than 1 year. Needless to say, a cell obtained after subculturing is also within the scope of the present invention, as long as the requirements of the present invention are met. Since the isolated human cell according to the present invention is originated from a transformed human kidney cell line, the isolated human cell according to the present invention obtained by the method described below is usually a cell of a cell line which can be subcultured for a long period of time of not less than 1 year.

Among the isolated human cell according to the present invention obtained in the Example described below, as a cell which is especially excellent in the growing ability and ability to grow HVJ, GIC20 cell was obtained. GIC20 cell has been deposited with International Patent Organism Depositary, National Institute of Advanced Industrial Science and Technology (Address: AIST Tsukuba Central 6, 1-1-1 Higashi, Tsukuba, Ibaraki, Japan), under accession No. FERM BP-10399 as of Aug. 11, 2005, under the Budapest Treaty.

The isolated human cell according to the present invention can be obtained by a method for obtaining a human cell, the method comprising the steps of suspension-culturing a human transformed kidney cell line in a serum-free medium, and cloning the grown cells; and selecting, from the cloned cells, a cell whose doubling time in logarithmic growth phase in suspension culture in a serum-free medium is not more than 40 hours, which has a freeze-recovery property, whose maximum density of viable cells in suspension culture is not less than $10^6$ cells/mL, in which HVJ can grow.

The suspension culture in the serum-free medium can be carried out as described above, and preferably, a suspension culture in a culture medium suited for the growth of 293 cells, such as the above-described T6 medium, at 36.5° C., under 5-10% $CO_2$, and more preferably in a gyratory culture at 100-120 rpm. The parent cell line is usually plate-cultured in a serum-containing medium. As a method for changing the culturing to the suspension culture in a serum-free medium, the direct adaptation method can preferably be employed. The direct adaptation method is one of the methods of acclimatization by which cells cultured in the presence of serum are changed to those which can be cultured in a serum-free medium. The direct adaptation method is not a method in which the serum concentration is gradually lowered to acclimatize the cells, but a method in which the serum-containing medium is completely removed by centrifugation or the like, and the cells are directly suspended in a serum-free medium to start the culturing, thereby acclimatizing the cells. By this method, since only the cells which can be adapted to a drastic change in the environment of the culturing survive, it is expected that a strong cell line may be obtained. It should be noted, however, as long as an isolated human cell which satisfies the requirements of the present invention can be obtained, other culturing conditions may also be employed. For example, other serum-free media used in the culturing of 293 cells may be employed, the culturing temperature may be changed within the range of, for example, 32° C. to 38° C., or the culturing may be carried out under an appropriate $CO_2$ atmosphere.

The cells grown by the suspension culture in the serum-free medium are collected and cloned. The cloning can be attained by separating the cells to single cells under the microscope, and growing each of the separated single cells from one cell by making the cell divide. In the step of growing the cells from one cell, serum may be added to the medium in order to aid the growth, and preferably, serum in an amount of 20 to 30% by weight is added. Further, to aid the growth, static culture on a plate is preferably employed in this step. After growing the cells, the medium is slowly returned to the serum-free medium, and the cells are suspended. Since each of the separated single cells is one which can be suspension-cultured in the serum-free medium, the cells after the growth can also be suspension-cultured in the serum-free medium. Since the cell population after the growth is a clone originated from a single cell, it is an isolated cell population which does not contain cells originated from other cells.

Thereafter, from the obtained clones, the clone(s) which satisfy(ies) the above-described various characteristics defined in the present invention is(are) selected. The method for measuring each of the characteristics is as described above, and also described in detail in the Example below. As for the ability to grow HVJ, it is preferred to select a clone which exhibits the ability as high as possible. In cases where a number of clones satisfying the requirements of the present invention are obtained, needless to say, it is preferred to select a clone which exhibits the better value for each of the characteristics. That is, it is preferred to select a clone whose doubling time in the logarithmic growth phase is shorter, the density of viable cells in suspension culture is higher, and the FFU of HVJ is higher. By the method described above, the human cell according to the present invention which satisfies the characteristics defined in the present invention can be obtained. Each selection may be carried out dividedly in two or more steps. More particularly, for example, it is possible to primarily select the clones which satisfy the requirements of the present invention, and then to secondarily select a clone(s) which exhibit(s) better characteristics under the same conditions or under more optimized conditions. Alternatively, in the primary selection, under the conditions which can be attained by simple operations, clones which exhibit excellent properties, for example, the clones which attained the results of top 10% or less are selected, and the clone(s) satisfying the requirements of the present invention are secondarily selected under more optimized conditions. For example, in the Example below, as for the ability to grow HVJ, the clones showing high ability in the static culture in a 96-well microplate are preliminarily selected, and then the secondary selection is performed using the ability to grow HVJ in the suspension culture as an index. Selection of the clones satisfying each characteristics may be carried out sequentially for the respective characteristics. Since the growing ability and the maximum density of viable cells are measured by measuring, with time, the density of viable cells in the suspension culture, the selections can be attained in a single step.

Since the isolated human cell according to the present invention was obtained employing the ability to grow HVJ as one of the indices, it can be used for the production of HVJ. Especially, since the cell of the present invention can be suspension-cultured in a serum-free medium, has a high growing ability, and can be cultured at a high density, it can be suitably employed for the mass production of HVJ. As the production conditions of HVJ, the conditions described above for the measurement of FFU are preferred. The grown HVJ can be purified by, for example, recovering the culture supernatant after removing the cells by filtration or centrifugation, and purifying the culture supernatant by column chromatography.

Further, since the cell of the present invention can be suspension-cultured in a serum-free medium, has a high growing ability, and can be cultured at a high density, it may be suitably used for the production of other viruses which can grow in the cell of the present invention, and for the production of recombinant proteins produced by a genetic engineering technique. Although an example of the other viruses which can grow in the cell of the present invention is adenovirus which will be concretely described in the Example below, the viruses are not restricted thereto.

Since the cell has a high growing ability by suspension culture, master cell bank comprising a plurality of vessels each of which comprises the cell can be easily prepared. As the vessel, for example, a vial made of glass or the like may be employed, although the vessel is not restricted thereto. The number of cells contained in each vessel is not restricted, and is usually about $5 \times 10^6$ cells to $5 \times 10^7$ cells. Since the cells included in the master cell bank are a clone, they have the same properties, which is convenient when the cells are used as a tool for analyzing gene function or as a vector for gene therapy.

As described above, since the isolated human cell according to the present invention can be suspension-cultured in a serum-free medium, has a high growing ability, can be cultured at a high density, can grow HVJ in the cell, and has a freeze-recovery property, it is advantageous for the mass production of HVJ and other viruses, recombinant proteins and the like. Especially, with the preferred cell such as one obtained in the Example below, since the ability to grow HVJ is high, the characteristics are not changed even if the cell is subcultured for a long time, and since the culturing can be easily scaled-up, the cell is especially advantageous for the mass production of HVJ and other viruses, recombinant proteins and the like.

The present invention will now be described more concretely by way of an example thereof. However, the present invention is not restricted to the example below.

Example

1. Obtainment of GIC20 Cell Line from 293 Cell (1) Acquisition of Cells 293 cells were acquired from JCRB (present Health Science Research Resources Bank (HSRRB) (number of subculturing: 37; doubling time: 62 hours). After waking the 293 cells, they were maintained by subculturing by adherent culture using MEM supplemented with 5% FBS.

(2) Preparation of Culture Media

As the culture media used for suspending the 293 cells and for changing the medium of 293 cells to a serum-free medium, respectively, those for suspending the 293 cells and for changing the medium of 293 cells to a serum-free medium, which have been commercialized or which are under development by manufacturers of media and reagents were obtained. Each of the media was used in accordance with the protocol recommended by the manufacturer, and L-glutamine was added to a final concentration of 4-8 mM. Further, Pluronic F-68 was added in an amount of 0.1-0.2% as required.

(3) Changing the Medium to Serum-Free, and Suspension and Acclimatization of Cells The 293 cells maintained by subculturing by adherent culture using a serum-containing medium were peeled by trypsin treatment, and collected by centrifugation. Acclimatization was tried by total replacement of the medium from the serum-containing medium to a serum-free medium by the direct adaptation method. Simultaneously with the replacement of the medium, the cells were seeded in an Erlenmeyer flask to a density of 3 to $5 \times 10^5$ cells/mL, and culturing of the cells by gyratory culture (100 rpm) using a rotary shaker in an incubator at 36.5° C. under 5-10% $CO_2$ was started. The change of the medium to a serum-free medium, and change of the culturing to suspension culture were tried using not less than 10 types of media. By continuing the maintenance culture of the cells whose growth after replacement of the medium was confirmed, the cells were gradually acclimatized to the serum-free medium. In the maintenance culture, the cells were seeded at a density of $3-5 \times 10^5$ cells/mL, and when the cell density reached $1 \times 10^6$ cells/mL after gyratory culture for several days, the culture medium was diluted with a fresh medium. T6 medium (trade name "EXCELL-293") produced by JRH Bioscience and HyQ PF-293 produced by HyClone showed particularly high growing ability.

Thus, using T6 and HyQ which showed good growing ability, the cells were cultured for a long time (not less than 30 days) to proceed the acclimatization of the cells to the serum-free medium. Comparing T6 and HyQ, T6 showed better growing ability and better suspending property. As for the cells acclimatized to T6, the acclimation culture was carried out for 140 days, and the resulting cells were subjected to the cloning described in the section below.

(4) Cloning of Cells

The cells which showed the best growing conditions and which were acclimatized to T6 medium were cloned. The cloning was performed by the limiting dilution method using a 96-well plate, and 838 single clones were confirmed under the microscope. To aid the growth from the single clones, culturing was started using a medium supplemented with serum in an amount of 20-30%. Static culture was performed in an incubator at 37° C. under 10% $CO_2$. While scaling up the culturing according to the growth of the cells, the serum concentration was gradually lowered to return the culturing conditions to serum-free and suspension culture. Using the freeze-recovery property, growing ability and HVJ productivity as indices by the methods described below, finally 45 types of cells originated from single colonies were obtained.

(5) Cryopreservation of Cells

During the acclimation culture and cloning, cells were cryopreserved. After scaling up the cells, the cells were centrifuged and suspended in a medium for freezing, which medium was prepared so as to attain a ratio of fresh medium: conditioned medium:DMSO (dimethyl sulfoxide) of 45:45:10, followed by dividedly placing the cells in vials in a population of $1 \times 10^7$ cells/vial. When freezing the cells, the thus prepared cell vials were set in a cryocontainer, and the cells were frozen in a freezer at −80° C. By using the cryocontainer, freezing at a rate of −1° C./minute which is said to be ideal in freezing cells can be achieved, so that the damage of the cells due to the freezing operation can be reduced. The vials frozen in the freezer at −80° C. were then transferred to a vessel containing liquid nitrogen and cryopreserved in the gas phase (−150° C.). The "fresh medium" used here was the medium to be used for the culturing, which had not been used, and the conditioned medium used here was the medium which had been used, that is, the culture supernatant. After the cryopreservation for not less than 3 days, the cells were thawed and subjected to the selection using the growing ability and HVJ productivity as indices.

(6) Selection of Highly Growing Clones

The growing ability was evaluated by suspension-culturing the cells in T6 medium at 36.5° C. under 5-10% $CO_2$, and measuring, with time, the density of viable cells with an automated cell viability analyzer Vi-CELL (registered trademark) of Beckman Coulter, thereby determining the doubling time in logarithmic growth phase. The cells having a doubling time of not more than 35 hours were selected. The maximum density of viable cells of each of the selected clones was not less than $4 \times 10^6$ cells/mL.

(7) Selection of Cells which Highly Produce Virus

An aliquot of each of the clones which showed good growing ability in the cloning was sampled during the step of scaling up, and HVJ production test was performed for selecting the cells which highly produce the virus.

(i) Method of Production of HVJ

HVJ was produced by adding to the cells 2-8 μg/mL (final concentration) of trypsin and HVJ (multiplicity of infection: MOI=23) as a seed virus, and culturing the cells at 32-34° C. in a 5% $CO_2$ incubator for 2 to 3 days. After centrifugation, the supernatant was recovered and the HVJ production titer was measured.

(ii) Measurement of HVJ Production Titer

Figure 2:
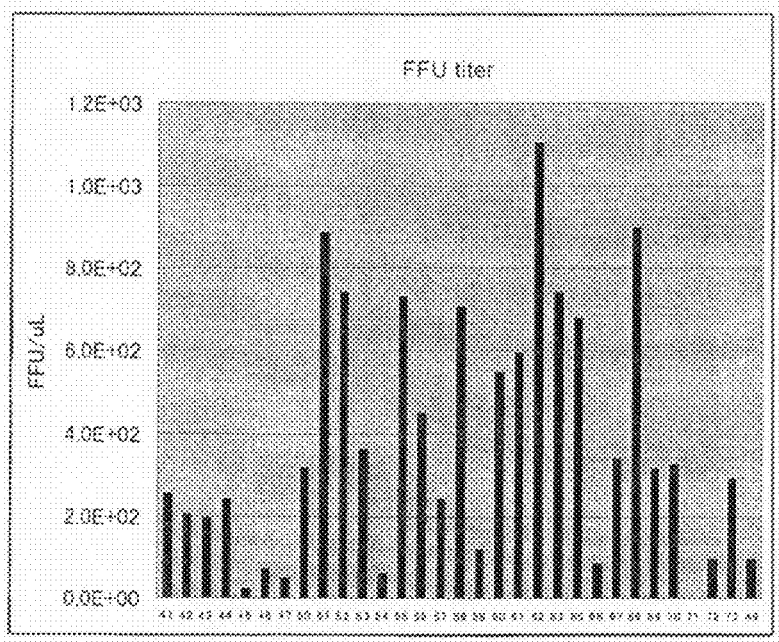
FIG. 2 HVJ Production Test of Single Clones during Cloning.

The amount of the produced HVJ was measured by HA test (hemagglutination test: the physical number of virus particles is measured by measuring the hemagglutination ability of the HA protein on the HVJ viral membrane), NA test (neuraminidase activity test: the physical number of virus particles is measured by measuring the neuraminidase activity of the HA protein on the HVJ viral membrane) or FFU test (fluorescent antibody method: infectious HVJ is quantified by counting the number of infected cells). (Reference: Virus Experimental Protocols, Medical View Co., Ltd., 1995, 68-78; The sialic acids J. Biol. Chem., 240, 3501 (1965)). As an example, the results of the measurement of production titer determined by the FFU test are shown in FIG. 2. Clones showing various productivities had been obtained. These tests were carried out concretely as follows:

HA Test: Stored chicken blood and PBS(−) were mixed by upside-down mixing to prepare a 10% suspension of chicken red blood cells. The HVJ production sample to be measured was thawed and placed in a 96-well plate, followed by serial dilution with PBS(−). Then the 10% chicken red blood cell suspension was diluted to 0.5% with PBS(−), and the resulting dilution was added to the plate so as to be mixed with the HVJ sample, followed by allowing reaction at 4° C. for 2 hours. Two hours later, the plate was visually observed, the well in which the HVJ concentration was the lowest and in which the red blood cells were agglutinated was determined, and the HAU was calculated from the dilution ratio.

NA Test: The HVJ production sample to be measured was thawed and placed in a 96-well plate, followed by serial dilution with Reaction Buffer. After preincubation at 37° C. for 1 minute with a plate heater, 15 μL each of the substrate 4-MU-nana was added, and the resultant was incubated at 37° C. for 15 minutes. The reaction was stopped by adding 60 μL each of Stop Buffer, and the fluorescence intensity was measured with a plate reader (Excitation: about 350 nm, Emission: about 460 nm). From the obtained values, using a standard curve of 4-MU, the concentration of the measured sample was calculated.

FFU Test: One day before the test, cells (LLC-MK2) for infection were seeded in a 24-well plate, and cultured in a $CO_2$ incubator. The HVJ production sample to be measured was thawed, and $10^2$-fold to $10^4$-fold diluted sample dilutions were prepared using PBS(+)/1% BSA. LLC-MK2 cells were removed, the medium was replaced with PBS(+)/1% BSA, and the prepared HVJ dilutions were added. After centrifugation twice at 3000 rpm, at 32° C. for 30 minutes using a plate centrifuge, the virus dilution (supernatant) was removed, and the medium was replaced with MEM-E/1% BSA, followed by culturing for infection at 37° C. under 5% $CO_2$ atmosphere for 16 to 24 hours. On the next day, the plate was taken out, each well was washed with PBS(−), and fixation of the cells was carried out with acetone/methanol (volume ratio: 1:1). Then a primary antibody solution was added, and incubation with shaking at 37° C. for 1 to 2 hours, or incubation at 4° C. for 16 to 24 hours was performed, thereby allowing the HVJ-infected cells to react with the primary antibody. After washing, a secondary antibody solution was added, and incubation with shaking was performed at 37° C. for 1 to 2 hours. By observation under a fluorescence microscope, the number of infected cells (green fluorescence is observed only in the cytoplasm, and the nucleus is seen in black as if it is dropped off) was counted, and FFU titer was calculated.

Figure 3:
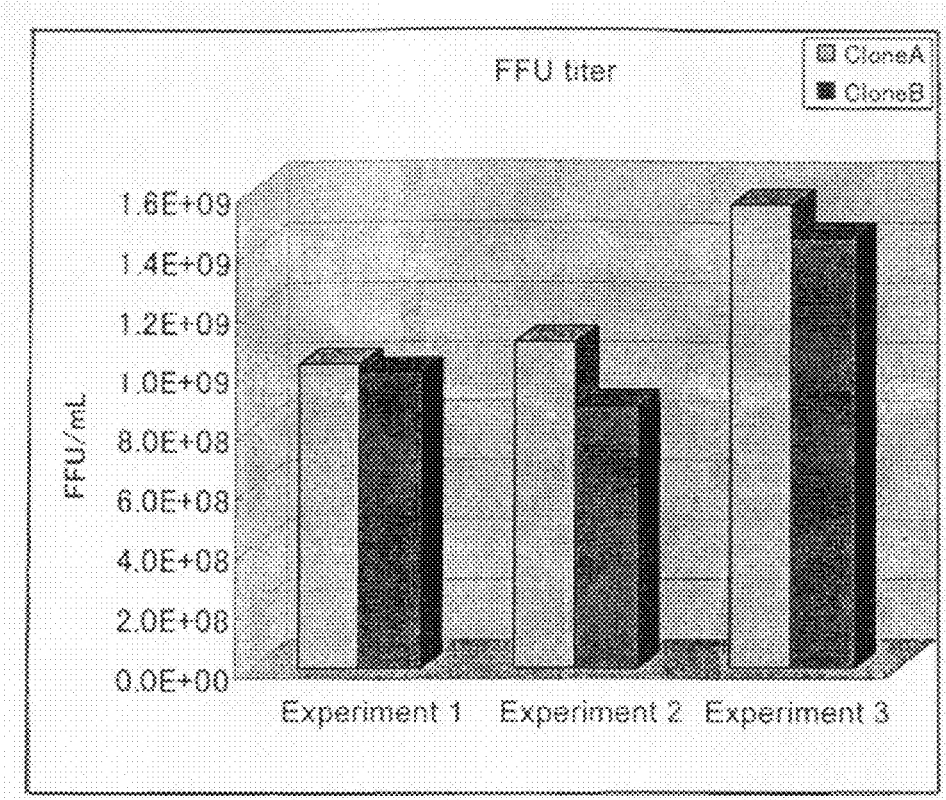
FIG. 3 HVJ Production by Bioreactor.

Two clones (Clone A and Clone B) which showed high growing ability and productivity were selected, and production of HVJ was carried out using a bioreactor. The production in the bioreactor was carried out at a scale of 1 L, and production culture was carried out in T6 medium in the presence of 2 mM butyric acid and 4 μg/mL of trypsin, at HVJ MOI=10, while controlling the culture conditions such that the stirring rate was 30 rpm, the temperature was 32° C., the DO (dissolved oxygen level) was 15%, and pH was less than 7.2. Forty two hours after the infection, the harvest material was recovered by centrifugation, and the titer was measured by the FFU test. As a result, Clone A showed a little higher productivity (FIG. 3).

(8) Measurement of Gene Transfection Activity (TF Activity) of Obtained HVJ

Figure 4:
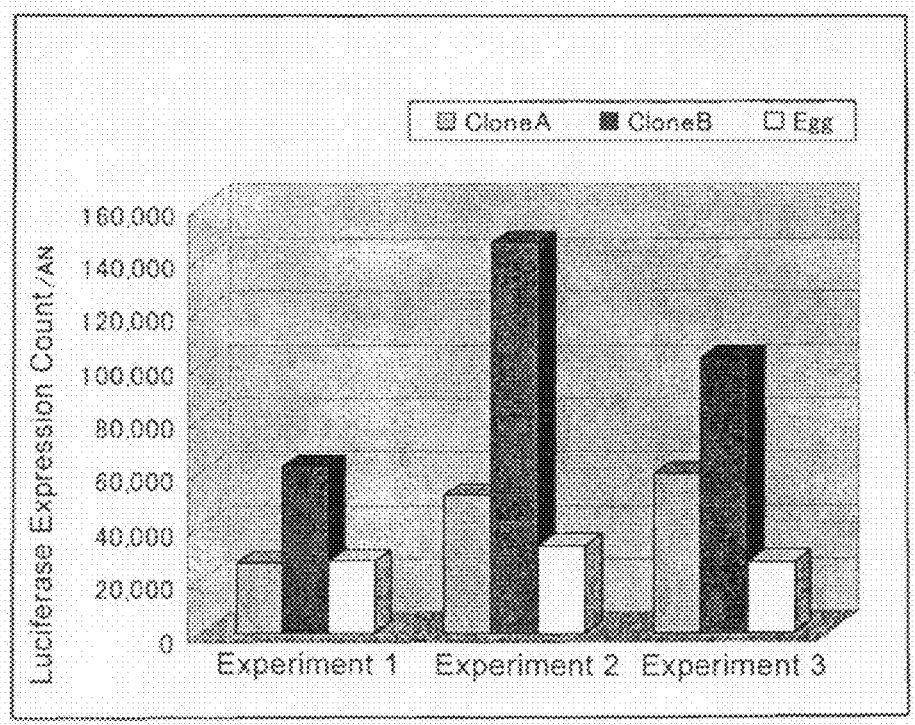
FIG. 4 Gene Transfection (TF) Activity.

The gene transfection activities of the HVJ produced by the above-described two clones (Clone A and Clone B) in the above-described bioreactor, and obtained after purifying the harvest material to remove impurities, were compared. As a control for comparison, HVJ (Egg) proliferated in an egg and purified in the same manner was tested. HVJ and a luciferase gene-expressing plasmid (pGL3) were transfected to BHK-21 cells. The transfection was carried out by a method wherein the HVJ-E and the pGL3 to be introduced were treated with a surfactant, the resultant was centrifuged, thereby pGL3 was encapsulated into HVJ-E, and the resultant was added to the cells subjected to transfection, thereby introducing it to the cells utilizing the cell fusion ability of the HVJ. Twelve to 24 hours after the gene transfection, relative luminescence unit (RLU) was measured using luciferase assay reagents. As a result, Clone B showed higher gene transfection activity than Clone A, and both of them showed higher activity than the virus of the control for comparison, which was proliferated in the egg (FIG. 4).

As described above, a number of clones having different growing ability and virus productivity were obtained by acclimatizing the cells to the serum-free medium, and cloning the suspended cells. Among the thus obtained clones, the clone (Clone B) which had excellent both growing ability and virus productivity, and which had an especially high gene transfection activity was named GIC20. As described above, GIC20 has been deposited with International Patent Organism Depositary, National Institute of Advanced Industrial Science and Technology, at AIST Tsukuba Central 6, 1-1-1 Higashi, Tsukuba, Ibaraki, Japan, under accession No. FERM BP-10399 as of Aug. 11, 2005, under the Budapest Treaty.

2. Analysis of Characters of GIC20 Cell (1) Growing Ability

Figure 5:
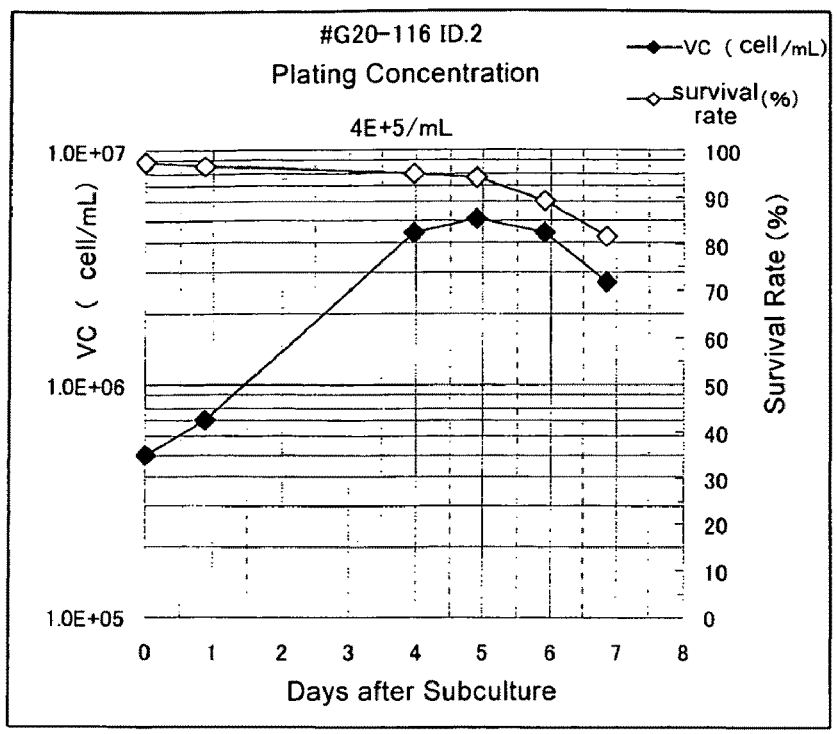
FIG. 5 shows the growing ability of the cells (batch culture) of the clone (GIC20) selected in the Example of the present invention. VC means viable cells.

The growing ability in a batch culture, of the cell of the clone selected based on the HVJ producing ability was examined. The cells were seeded at a density of $4\times10^5$ cells/mL, gyratory culture (100-120 rpm) was performed at 36.5° C., in a 5% $CO_2$ incubator using a rotary shaker. An aliquot of the culture medium was sampled and the number of cells was counted. The doubling time in the logarithmic growth phase (day 1 to day 4) was 28 hours, and the cell density reached the maximum density of $5\times10^6$ cells/mL at the 5th day from the start of the culturing. The cell counting was carried out using a automated cell viability analyzer Vi-CELL (registered trademark) of Beckman Coulter, in which the cells with a diameter of 12 to 20 μm were counted. The results are shown in FIG. 5.

Figure 6:
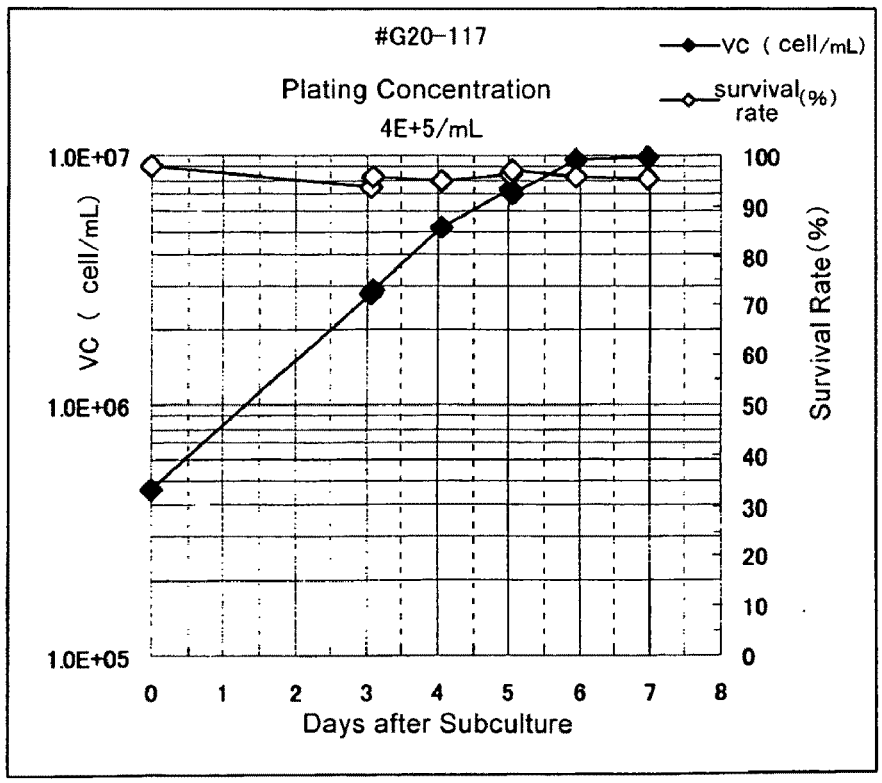
FIG. 6 shows the results of the test of the growing ability of the cells of the clone (GIC20) selected in the Example of the present invention. VC means viable cells.

Further, the growing ability in Fed Batch culture was also examined. In the same manner as described above, the cells were seeded at a density of $4\times10^5$ cells/mL, gyratory culture (100-120 rpm) was performed at 36.5° C., in a 5% $CO_2$ incubator using a rotary shaker. On day 3 and day 5, replacement of the medium was carried out by centrifugation. The doubling time in the logarithmic growth phase (day 1 to day 4) was 28 hours, and the cell density reached the maximum density of $1\times10^7$ cells/mL at the 7th day from the start of the culturing (FIG. 6).

(2) HVJ Production

Using the established highly virus-producing clone GIC20, the conditions for producing HVJ virus were optimized, and the HVJ-producing ability was tested. The cells for infection was grown to $2\times10^6$ cells/mL, a culture medium for infection supplemented with sodium butyrate (final concentration: 1-4 mM) and trypsin (final concentration: 2-8 μg/mL) was added in an amount of 30 to 50%, HVJ solution was added at an MOI of 1 to 10, and the cell were cultured at 32 to 34° C. for 40 to 44 hours, followed by recovering the culture supernatant by centrifugation. The recovered sample was dividedly placed in vessels and stored at −80° C. The measurement of the titer of the recovered HVJ sample was carried out by the method described above. As a result, the titers were: FFU=3.82E+9 FFU/mL, NA=289.1 mU/mL, and HA=1024 HAU/mL.

(3) Production of Adenovirus

The production ability of GIC20 to produce a virus other than HVJ was confirmed. The cells in the logarithmic growth phase at a density of $2\times10^6$ cells/mL was 2-fold concentrated by centrifugation and subsequent discarding of the culture supernatant, and an adenovirus vector (Adeno CMV-LacZ) was infected at an MOI of 2. After culturing for infection (gyratory culture at 100 rpm) at 37° C. in a 5% $CO_2$ incubator using a rotary shaker for 1 hour, equivolume of fresh medium was added, and the culturing for infection was continued. The supernatant was recovered 48 hours after infection, and the adenovirus titer was measured. The adenovirus vector produced by GIC 20 cells were purified using BD Adeno-X Virus Purification Kits (BD, Cat. No. 631533), and measured using BD Adeno-X Rapid Titer Kit (BD, Cat. No. 631028). As a result, the titer was $1.3\times10^9$ ifu/mL, or 185 ifu/cell in terms of the titer per cell. (The production per cell using the original 293 cells showing the highest titer was 120 ifu/cell).

Figure 7:
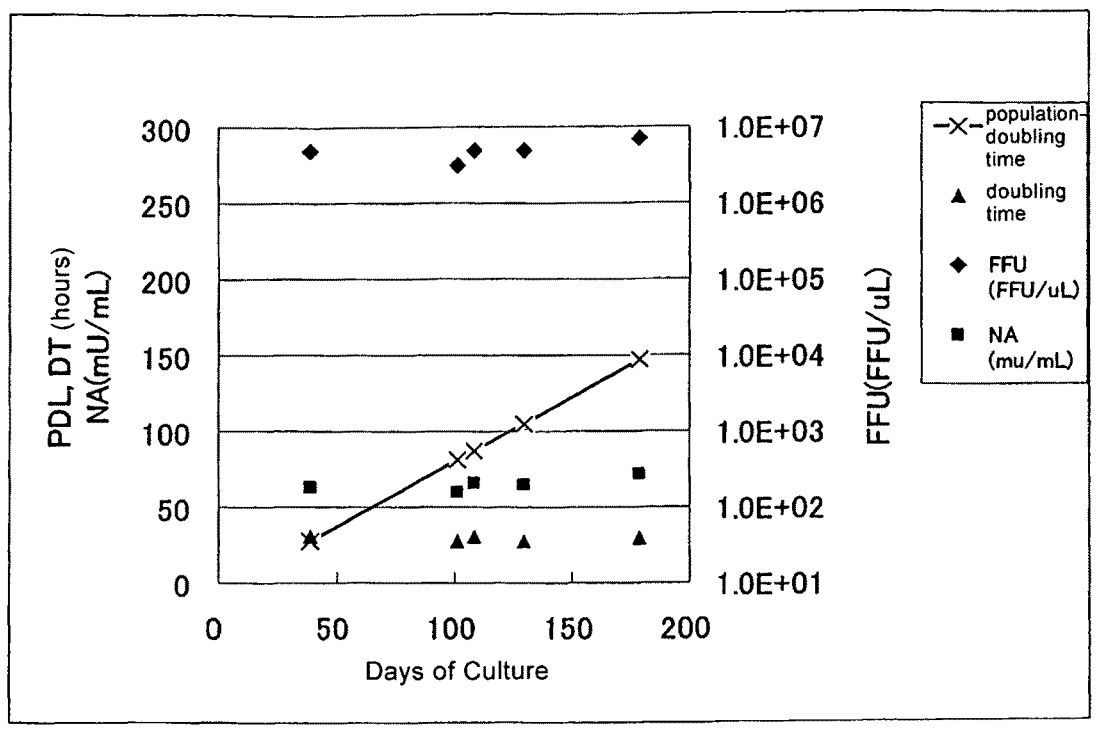
FIG. 7 shows the results of the measurements of the clone (GIC20) selected in the Example of the present invention over 6 months for its HVJ-producing ability (FFU titer and NA activity), cell-doubling time and the cell population-doubling time. "X" indicates the population-doubling time, "▲" indicates the doubling time, "♦" indicates the FFU titer and "■" indicates the NA activity.

Subculturing of GIC20 was performed for 6 months, and days 39, 102, 109, 130 and 179 after thawing, HVJ-producing ability (FFU titer and NA activity), the cell-doubling time and the cell population-doubling time were measured. No prominent change was observed when compared with the cells immediately after thawing after 6-month storing (FIG. 7). Thus, it was proved that the cell maintains the growing ability and virus-producing ability for at least 6 months.

The invention claimed is:

1. The cell GIC20, deposited under accession number FERM BP-10399.

2. A method of producing Hemagglutinating Virus of Japan (HVJ virus) comprising:
   a) infecting GIC20 cells, deposited under accession number FERM BP-10399, with said HVJ virus;
   b) growing said HVJ virus in said GIC20 cells in culture medium; and
   c) recovering said HVJ virus.

3. The method of claim 2, wherein said GIC20 cells are inoculated in step a) by adding HVJ virus and a medium for infection to a culture of said GIC20 cells.

4. The method of claim 3, wherein said medium for infection comprises sodium butyrate and Factor-Xa or trypsin 10 and is added to said culture medium to a concentration of 30 to 50%.

5. The method of claim 3, wherein said HVJ virus is added to said GIC20 cells at MOI of 1-10.

6. The method of claim 2, wherein said HVJ virus is recovered by removing said GIC20 cells from said culture medium by filtration or centrifugation and purifying the HVJ virus by column chromatography.

7. The method of claim 6, wherein said GIC20 cells are inoculated in step a) by adding HVJ virus and a medium for infection to a culture of said GIC20 cells.

8. The method of claim 7, wherein said medium for infection comprises sodium butyrate and Factor-Xa or trypsin 10 and is added to said culture medium to a concentration of 30 to 50%.

9. The method of claim 7, wherein HVJ virus is grown in said GIC20 cells in culture at 30 to 34° C. for 40 to 72 hours.

10. A method of producing adenovirus comprising:
   a) infecting GIC20 cells, deposited under accession number FERM BP-10399, with said adenovirus;
   b) growing said adenovirus in said GIC20 cells in culture medium; and
   c) recovering said adenovirus.

* * * * *